(12) United States Patent
Chiodo

(10) Patent No.: US 6,415,679 B1
(45) Date of Patent: Jul. 9, 2002

(54) MANUAL DRIVE FOR POSITIONING PRECISION INSTRUMENTS

(76) Inventor: Chris D. Chiodo, 29277 Newport, Warren, MI (US) 48093

( * ) Notice: Subject to any disclaimer, the term of this patent is extended or adjusted under 35 U.S.C. 154(b) by 0 days.

(21) Appl. No.: 09/707,051

(22) Filed: Nov. 6, 2000

(51) Int. Cl.[7] .......................... G05G 1/08; G05G 11/00; B25J 13/02
(52) U.S. Cl. .................. 74/490.15; 74/10.54; 74/89.29; 74/441; 74/665 D; 269/71; 359/392; 359/393
(58) Field of Search ................................ 74/10.54, 441, 74/490.14, 490.15, 89.29, 665 D; 269/71; 359/392, 393

(56) References Cited

U.S. PATENT DOCUMENTS

| | | | | |
|---|---|---|---|---|
| 1,503,553 A | * | 8/1924 | Powell | 116/254 |
| 1,625,094 A | * | 4/1927 | Reppert | 74/10.54 |
| 1,643,787 A | * | 9/1927 | Rottgardt | 74/10.54 |
| 3,019,705 A | * | 2/1962 | Wilkinson | 359/392 |
| 3,683,704 A | * | 8/1972 | Kuroha | 359/392 |
| 4,173,902 A | * | 11/1979 | Shio | 74/10.52 |
| 4,445,758 A | * | 5/1984 | Emmel | 359/392 |
| 4,676,608 A | * | 6/1987 | Faubion | 359/383 |
| 5,976,156 A | * | 11/1999 | Taylor et al. | 606/130 |

* cited by examiner

Primary Examiner—Allan D. Herrman

(57) ABSTRACT

A carriage adapted for carrying a laboratory instrument such as a pipette, electrode, or syringe is driven by a drive shaft in the form of a lead screw. The lead screw is selectively driven by a high speed drive wheel or by a low speed drive wheel. The drive wheels are coaxially mounted around the drive shaft and concentrically and coaxially arranged with respect to one another. The drive shaft and the two drive wheels all rotate in unison in the same rotary direction.

20 Claims, 4 Drawing Sheets

MANUAL DRIVE FOR POSITIONING PRECISION INSTRUMENTS

BACKGROUND OF THE INVENTION

1. Field of the Invention

The present invention relates in general to manually operated precision mechanical drives and in particular to an ergonomic dual gear drive system for use in laboratory equipment such as micromanipulators and stereotaxic systems.

2. Description of Prior Developments

Various experimental and investigative procedures are commonly performed on live test specimens such as laboratory animals. These animals, which are often rodents such as rats and mice, are typically secured in a rigidly fixed position during these procedures. It is often desirable to accurately position an instrument such as a pipette, potentiometer, electrode, probe, sensor, laser or other tool adjacent, on or within the specimen, in order to accurately induce and/or monitor various reactions and responses to certain stimuli or other inputs.

The instruments used in these procedures are typically mounted on mechanical slides which are manually driven along a slideway by a lead screw, rack and pinion or other similar drive. In order to operate the slide so as to move the instrument into position, an operator typically rotates a knob which is connected to a gear drive. The gear drive then drives the movable slide over a fixed slideway and thereby moves an attached instrument into and out of position.

In some positioning systems, only a single drive is provided to position an instrument along a slideway. This presents the instrument designer with a choice of using a relatively coarse or high gear ratio drive or a relatively fine or low gear ratio drive. Each type of drive has both advantages and disadvantages.

A high ratio drive allows an operator to quickly move an instrument along the slideway with relatively few turns of a drive knob. This is convenient for quickly moving an instrument from a position remote from a test specimen to a position close to the test specimen and vice versa.

However, such a coarse adjustment is difficult to manipulate so as to achieve small delicate and precision movements of the instrument once it is positioned close to the test specimen. That is, small movements of the rotary drive knob by an operator result in relatively large movements of the instrument, thereby making fine manual adjustments of the instrument difficult to achieve.

If a low ratio drive is provided instead, precision movements and adjustments of the instrument are facilitated, but large movements of the instrument along the slideway are time consuming and inconvenient That is, an operator must complete many turns on the drive knob in order to move the slide and its attached instrument any appreciable distance along the slideway.

It is possible to provide two separate drives for driving an instrument into position. One drive can be a coarse, high speed drive and the other a fine, low speed drive. The first drive can be driven by a first manually operated rotary knob which drives a relatively coarse pitch lead screw drive and the second drive can have a separate, remotely positioned manually operated drive knob which turns a relatively fine pitch lead screw drive.

With two separate drives, an instrument can be brought into close proximity to a test specimen by the high speed, high gear ratio drive, and then an operator can switch over to manipulating a low speed, low gear ratio drive for achieving accurate, final positioning of the instrument.

While a dual drive positioning system of the type noted above can provide both coarse and fine movements of an instrument along a slideway, an operator is somewhat inconvenienced by the required hand movement over some considerable distance from one drive knob to another. That is, the operator's hand must be moved from one position to another at spaced apart locations on the apparatus to move from one drive knob to another.

This can be distracting to the operator as the operator's attention must often be intensely focused on the position of the instrument relative to the test specimen. This attention can be broken if the operator has to look away from the instrument to find the other drive knob.

Accordingly, a need exists for an ergonomic dual drive system for quickly and accurately positioning an instrument relative to a test specimen.

A further need exists for such a dual drive system which allows an operator to quickly move an instrument into a desired position with a high speed coarse drive and to subsequently accurately position the instrument into a final position with a low speed fine precision drive.

Yet a further need exists for such a dual drive system which allows an operator to manually switch between coarse and fine instrument drives without the necessity of moving the operator's hand over any significant distance which would otherwise distract the operator from the precision adjustment of the instrument relative to a specimen.

Still a further need exists for such a dual drive system which includes a pair of drive knobs ergonomically arranged so as to allow an operator to selectively manipulate each drive knob without the need for moving the operator's focus from the instrument and specimen to the drive knobs.

SUMMARY OF THE INVENTION

The present invention has been developed to fulfill the needs noted above, and therefore has as an object the provision of a dual drive system for manipulating positioning apparatus, particularly laboratory apparatus such as precision slides and slideways for moving various instruments and tools into position relative to a workpiece or other specimen such as a laboratory test animal.

A further object of the invention is the provision of a dual drive manipulator which includes a high speed coarse drive and a low speed fine drive, each having a drive knob located ergonomically with respect to the other.

Yet another object of the invention is the provision of such a dual drive manipulator which has a pair of drive knobs coaxially arranged in close proximity so as to allow an operator to maintain a substantially fixed hand position while switching between coarse and fine drives using small, comfortable finger and thumb movements.

Another object of the invention is the provision of a dual drive precision slide for precision instruments which allows an operator to maintain fixed eye focus on the instrument while switching between coarse and fine drives.

Still another object of the invention is the provision of a dual drive manipulator having a high speed or coarse adjustment knob and a low speed or fine adjustment knob each geared to the same single drive screw to avoid tolerance build up associated with multiple drive screw manipulators.

Another object of the invention is the provision of a precision mechanical manipulator having a pair of coaxially mounted drive knobs arranged coaxially with a single drive shaft or lead screw.

A further object of the invention is to provide a manipulator with a dual drive driven by a pair of rotary drive knobs which, when turned in the same direction, (clockwise or counterclockwise) each drives a slide in the same direction (forward or backward). This reduces operator error and potential confusion as to which knob drives the slide in what direction when turned and rotated in a given direction.

These and other objects are met in accordance with the present invention which is directed to a dual gear drive system for moving and positioning tools, sensors or other instruments along a slideway of a precision positioning instrument. The dual gear drive has found particular advantage in laboratory equipment such as micro-manipulators and stereotaxic apparatus.

An important feature of the invention is the coaxial mounting of a low speed or fine rotary drive knob closely adjacent to a high speed or coarse rotary drive knob. The fine rotary drive knob can be mounted closely axially adjacent to the course rotary drive knob to minimize the distance required to move one's finger and thumb from one knob to the other. This, in turn, allows an operator to maintain eye focus on an instrument and specimen as the operator moves from one drive knob to the other. No gross hand movements are required.

The aforementioned objects, features and advantages of the invention will, in part, be pointed out with particularity, and will, in part, become obvious from the following more detailed description of the invention, taken in conjunction with the accompanying drawings, which form an integral part thereof

BRIEF DESCRIPTION OF THE DRAWINGS

In the drawings.

In the various views of the drawings, like reference numerals designate like or similar parts.

DETAILED DESCRIPTION OF THE PREFERRED EMBODIMENTS

Figure 1:
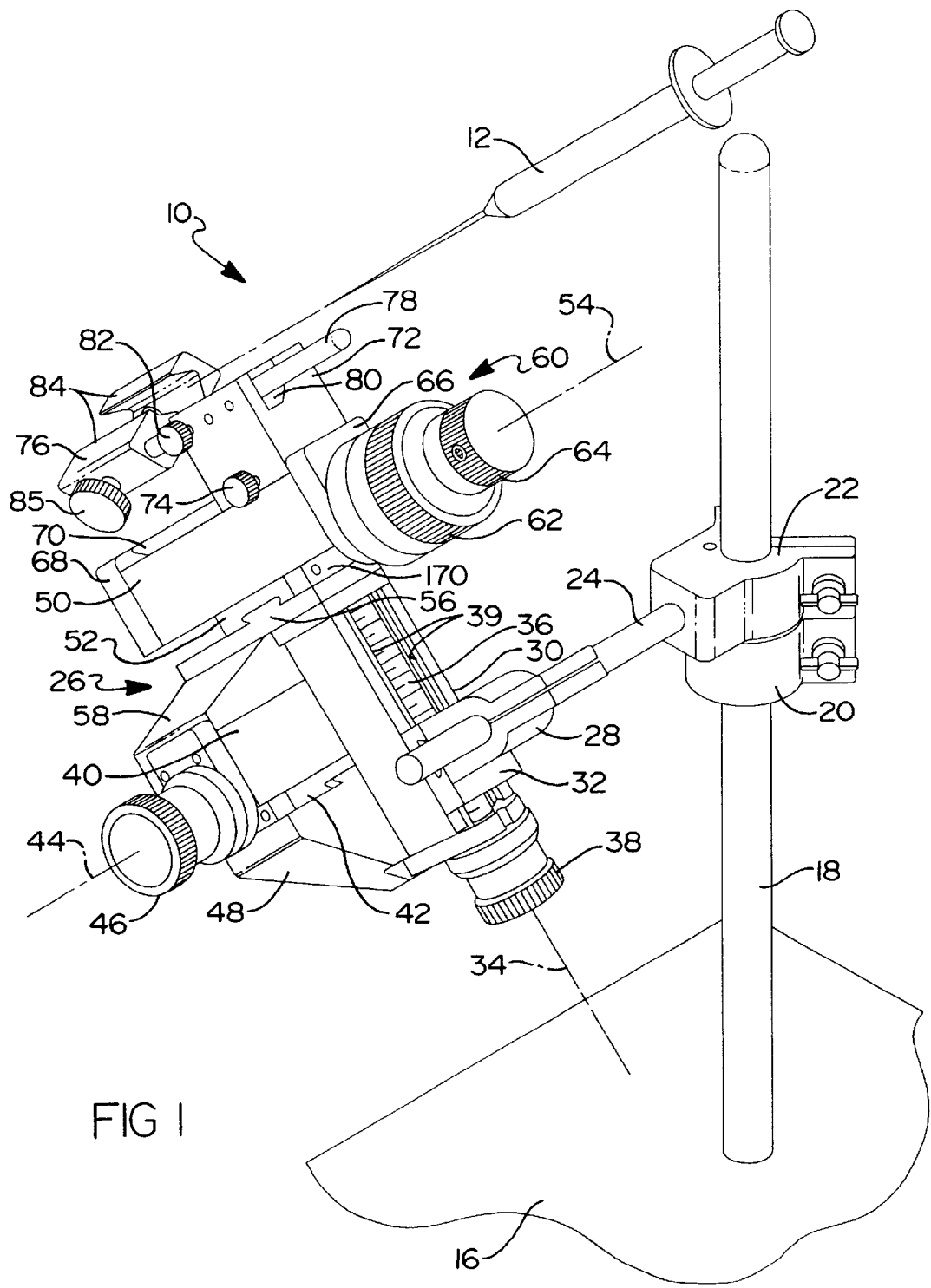
FIG. 1 is a schematic perspective view of a portion of a laboratory apparatus fitted with a dual drive positioning system constructed in accordance with the invention.

The present invention will now be described in conjunction with the drawings, beginning with FIG. 1 which shows as an example, a precision laboratory positioning apparatus 10, sometimes referred to as a micromanipulator. Apparatus 10 is used as a precision positioning system for accurately positioning an instrument 12, such as a syringe, with respect to a specimen such as a laboratory animal.

Apparatus 10 includes a fixed weighted base 16 to which a vertical support rod 18 is anchored. A pair of adjustable clamps 20, 22 is provided to allow for adjustable sliding movement of clamp bar 24 along the vertical rod 18. A three axis tool positioning slide assembly 26 is clamped to the free end of bar 24 in a known fashion with an adjustable clamp 28. The slide assembly 26 includes three individual slides and slideways mutually orthogonally interconnected to allow the instrument 12 to be moved along three mutually perpendicular directions.

For the purpose of explanation, a first slide 30 is movably mounted on a first slideway 32 to provide movement to slide assembly 26 along an "x" axis 34. Lead screw 36, which extends along the x axis 34, engages and drives assembly 26 via engagement with a rack of fixed gear teeth on the underside of slideway 32. Alternatively, the lead screw can be engaged with an intervally threaded drive nut fixed to the underside of slideway 32.

Knob or dial 38 is directly connected to lead screw 36 for a one-to-one drive ratio according to conventional practice. Projections or tongues on the underside of slideway 32 ride in grooves 39 in slide 30. Instead of a rack of teeth on the bottom of slide 32, a simple threaded bore can be provided for receiving each screw 36.

A second slide 40 is likewise movably mounted to a second slideway 42 to provide movement to the slide assembly 26 along a "y" axis 44 which is orthogonal to the x axis 34. The second slideway 42 is substantially the same as the first slideway 32 in that it is provided with a threaded bore or a linear rack of gear teeth which mesh with a lead screw driven directly on a one-to-one ratio by a rotary knob 46. Slideway 42 is fixed to a mounting block 48 which is in turn fixed in position to the underside of the first movable slide 30.

A third slide 50 is movably mounted to a third slideway 52 such as by a dovetail or tongue and groove to provide movement to the slide assembly 26 along a "z" axis 54 which is orthogonal to both the x and y axes 34, 44. Slideway 52 is modified in accordance with the invention as discussed further below.

A dovetailed plate 56 is fixed in position on a mounting block 58 which is in turn fixed in position on the second slide 40. Slideway 52 is fixed in place on the dovetailed plate 56 along a dovetailed groove which complements the dovetail on plate 56. As detailed below, a dual drive system 60 is provided for driving the third slide 50 over slideway 52. Drive system 60 includes a coarse rotary drive knob 62 and a fine rotary drive knob 64 coaxially mounted with the coarse knob around a common drive shaft or lead screw.

The third slide 50 has a support plate 66 fixed on one proximal axial end portion and an end cap 68 fixed on the opposite distal axial end portion. A dovetail slideway 70 extends along the top surface of the third slide 50 for guiding and supporting a mounting block 72 having a dovetail groove receiving the dovetail slideway 70. The mounting block 72 may be fixed in place along slideway 70 with a set screw 74.

Figure 2:
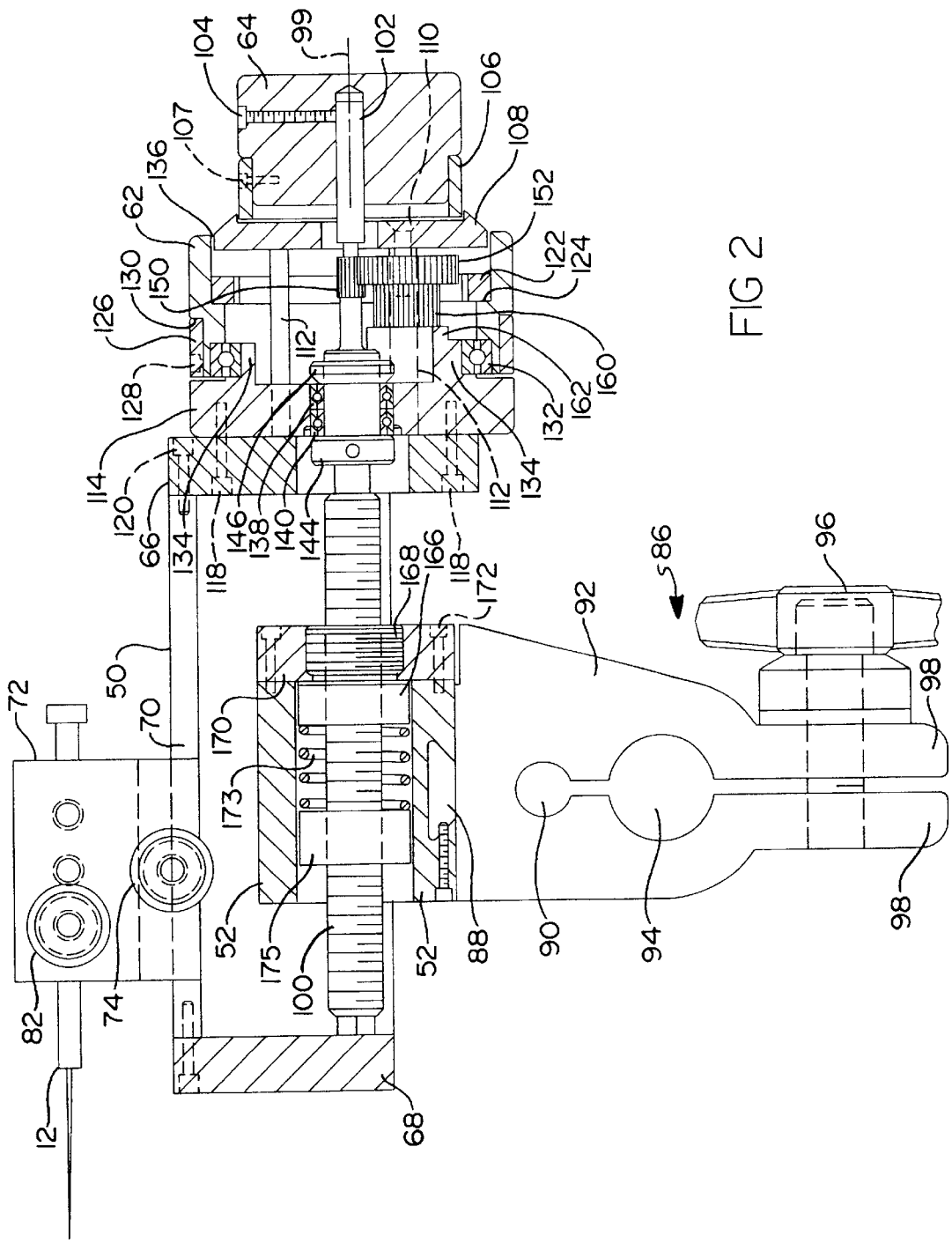
FIG. 2 is a view in axial section taken through a dual drive system of the type shown in FIG. 1.

A tool clamp 76 is adjustably mounted to the mounting block 72 via mounting bar 78. Mounting bar 78 is slidably received in a groove or channel 80 in the mounting block and fixed in position with set screw 82. A tool, probe or instrument 12 is received within the jaws 84 of clamp 76 and held in a fixed position with clamp set screw 85. In some cases, tool 12 can be directly held in mounting block 72 as shown in FIG. 2.

It can be appreciated that gross adjustments of tool 12 can be made with movement of the clamp bar 24, up and down rod 18, and by relatively coarse adjustment along the x and y axes made by turning knobs 38 and 46, respectively. Additional gross adjustment of the position of tool 12 can be made along the z axis by sliding mounting block 72 along the top of the third slide 50 as well as by sliding mounting bar 78 back and forth within channel 80. Finally, tool 12 itself can be moved within jaws 84 along the z axis for additional gross adjustment.

Tool 12 can be further moved along the z axis by turning the rotary drive knob 62 for a relatively coarse setting.

Rotary drive knob 64 can provide a fine precision movement of tool 12 along the z axis. Although only the third slide 50 is provided with a dual drive positioning system 60, the second and/or first slides 40 and 30 can also be provided with similar dual drive positioning systems, if desired.

Details of the dual drive positioning system 60 are shown in FIG. 2. System 60 may be clamped to the dovetailed plate 56 via slideway 52 as shown in FIG. 1, or alternatively clamped to a manual clamp assembly 86 as shown in FIG. 2. Clamp assembly 86 includes a dovetail 88 for sliding into the dovetail groove in slideway 52. A small split bore 90 is provided in clamp block 92 for clamping around small diameter support rods such as clamp bar 24 and a large split bore 94 is likewise provided for clamping around larger diameter support rods such as vertical rod 18. A winged rotary clamp screw 96 is threaded through the open jaws 98 of the clamp block 92 to provide clamping pressure within the split bores 90, 94.

Turning now to the details of the dual drive positioning system 60, it is seen in FIG. 2 that both the coarse rotary drive wheel or knob 62 and the fine rotary drive wheel or knob 64 are mounted coaxially with one another and coaxially around the axis 99 of a drive member such as a threaded drive shaft or lead screw 100. Other drive members can include rack and pinion drives and gear and pinion drives including worm gear drives. The fine drive wheel 64 is fixed on one end portion 102 of the drive shaft 100 by a set screw 104.

A fine adjustment calibration ring 106 is fixed around the outer circumference of the fine drive wheel 64 with a set screw 107. The inner axial end of the calibration ring 106 is concentrically nested with a close rotary clearance fit within a shallow circular recess formed in the outer surface of a stationary annular cover plate 108. The cover plate 108 is fixed in position by threaded screws 110 which hold the cover plate to the outer ends of three axially-extending anchor posts 112, two of which are shown in FIG. 2.

The inner ends of the anchor posts 112 are held by press fits within bores formed in a stationary annular bearing housing 114. The bearing housing is fixed in place against the support plate 66 with screws 118, and the support plate 66 is fixed to the third slide 50 by screws 120.

In this manner, the cover plate 108, which may be marked with one or more calibration ticks, is rigidly fixed in position along with the bearing housing 114, support plate 66 and the third slide 50. As described below, each of these members moves axially in unison when either of the knobs 62, 64 is rotated.

An internally fluted or toothed gear ring 122 is fixed within an internal annular step 124 formed on the inner surface of the coarse or high speed rotary drive wheel 62. Adhesive or set screws can be used to hold the gear ring 122 within drive wheel 62. A coarse adjustment calibration ring 126 is fixed with a set screw 128 within an annular step 130 formed on the outer surface of this coarse drive wheel 62.

The coarse drive wheel 62 is fixed to the outer race of a ball bearing 132 which has its inner race adhesively bonded or otherwise fixed to an axially extending annular boss or sleeve 134.

Boss 134 is formed on the outer end of the bearing housing 114. This mounting allows the course drive wheel 62 and its internal gear ring 122 to be smoothly rotated around the bearing housing. A small radial clearance 136 is maintained between the rotary drive wheel 62 and the fixed cover plate 108.

The drive shaft or lead screw 100 is rotatably mounted within bearing housing 114 with a pair of ball bearings 138, 140 which are press fit and adhesively bonded within a central bore formed through the bearing housing. The portion of the drive shaft journaled within the bearings 138,140 is held axially in place between a flange or collar 144 formed on or pinned to shaft 100, and a conical nut 146 threaded over the outer axial end of the journaled portion of shaft 100.

Nut 146 applies axial pressure only to the inner race of bearing 138 to preload the bearing assembly. The journaled portion of shaft 100 is press fit into the inner races of bearings 138,140.

Figure 3:
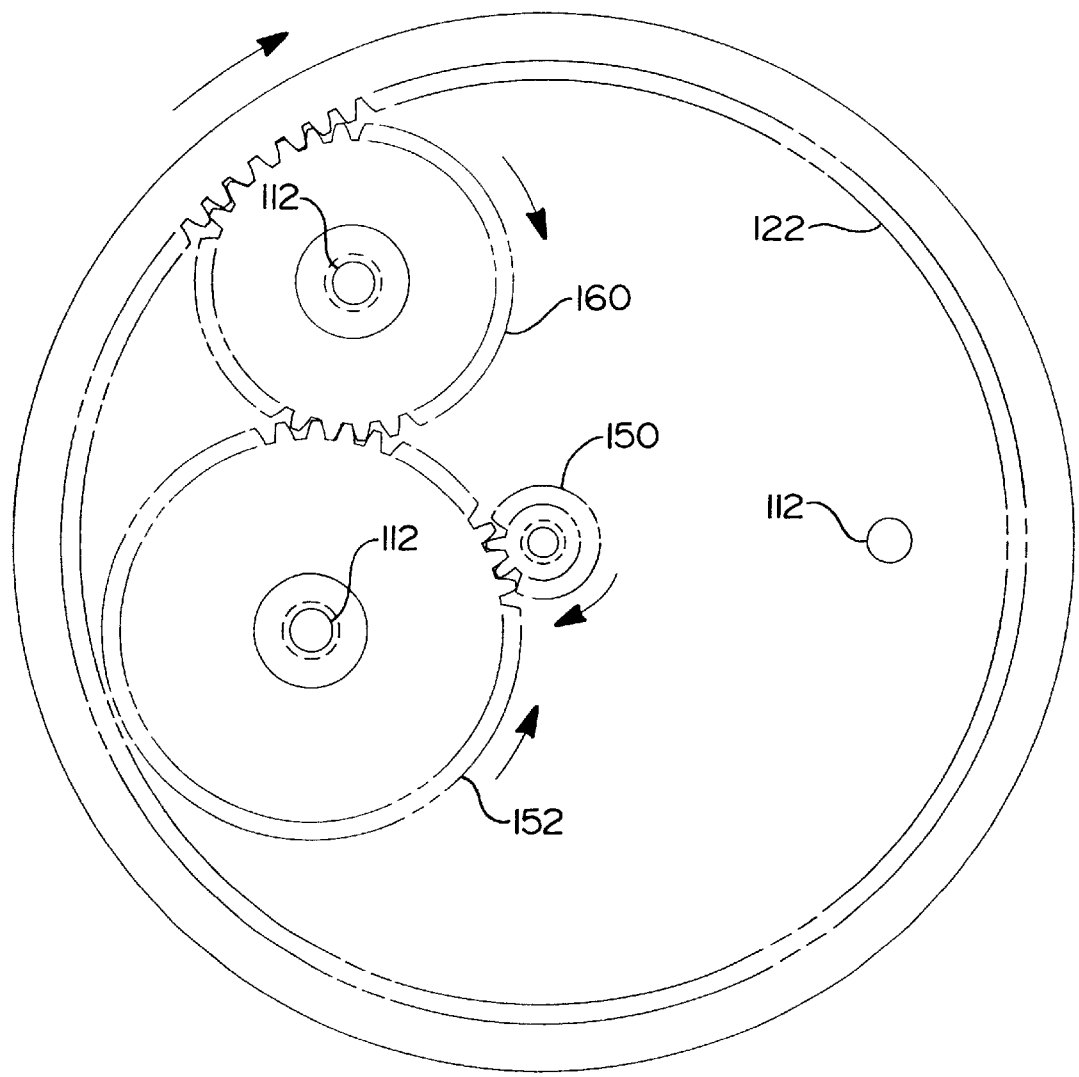
FIG. 3 is a schematic top plan view of the gear arrangement of the dual drive system of FIG. 2.

An axially fluted pinion gear 150 is cut into or otherwise separately mounted on the shaft 100 adjacent its outer end portion 102. As seen in FIGS. 2 and 3, pinion gear 150 meshes with an intermediary or idler gear 152 which is rotationally mounted on the end of one of the fixed anchor posts 112. The idler gear is axially restrained between the stationary (non-rotating) anchor post 112 and the stationary (non-rotating) cover plate 108.

The idler gear 152 is also in constant driving meshed engagement with a spur gear 160 which is rotationally mounted on a separate anchor post 112. Spur gear 160 is axially supported on one face against an axial boss 162 formed on the bearing housing 114 and axially held on anchor post 112 on its other face by the cover plate 108. The spur gear 160 is further in constant toothed engagement with the ring gear 122.

With the gear drive train described above, any desired gear ratios can be chosen to achieve the relative rotational drive speed of drive shaft 100. That is, in one embodiment, the pinion gear 150 has 10 teeth or flutes, and the ring gear has 100 teeth or flutes. This will provide a drive reduction of ten to one between the fine drive wheel 64 and the coarse drive wheel 62. The relative number of teeth on the idler gear 152 and spur gear 160 is not particularly critical or significant, as they will not affect the final gear drive ratio between knobs or wheels 64 and 62.

It should be noted from the directional arrows in FIG. 3 that rotation of either drive wheel 62, 64 in one direction rotationally drives the drive shaft in the same direction. This coordinated actuation is provided by the idler gear 152. This is ergonomically significant as noted above. When either of the drive wheels 62, 64 is rotated, they rotationally drive the drive shaft 100 in the same direction within a lead screw drive nut 166 mounted within slideway 52.

Drive nut 166 has an externally threaded end 168 which is threaded into a threaded bore formed through a lead screw or drive shaft mounting plate 170. The mounting plate 170 is fixed to slideway 52 with fasteners such as screws 172. A small clearance is maintained between the drive nut 166 and the internal walls of slideway 52 to allow the drive nut to be cantilevered inside the slideway. A spring 173 and nut 175 can be mounted on drive shaft 100 to reduce backlash in a known manner.

It can be appreciated that when the lead screw or drive shaft 100 is rotated by either drive wheel, i.e., directly at a 1:1 ratio by wheel 64 or at a higher drive speed ratio by wheel 62, the drive shaft 100 linearly advances to the left or moves backwards to the right as it rotates within drive nut 166. As the drive shaft 100 moves linearly, so does the entire third slide 50 along with any tool, instrument, instrumentation, sensor or other device attached to it.

It can be appreciated that the provision of ball bearings 132 for mounting the high speed drive wheel 62 on the bearing housing 114 provides extremely smooth rotation of the drive wheel 62. Moreover, ball bearings 138, 140 likewise provide extremely smooth rotation of the drive shaft 100 within the bearing housing 114. This gives the drive system a precision feel to the operator, which is most desirable.

Figure 4:
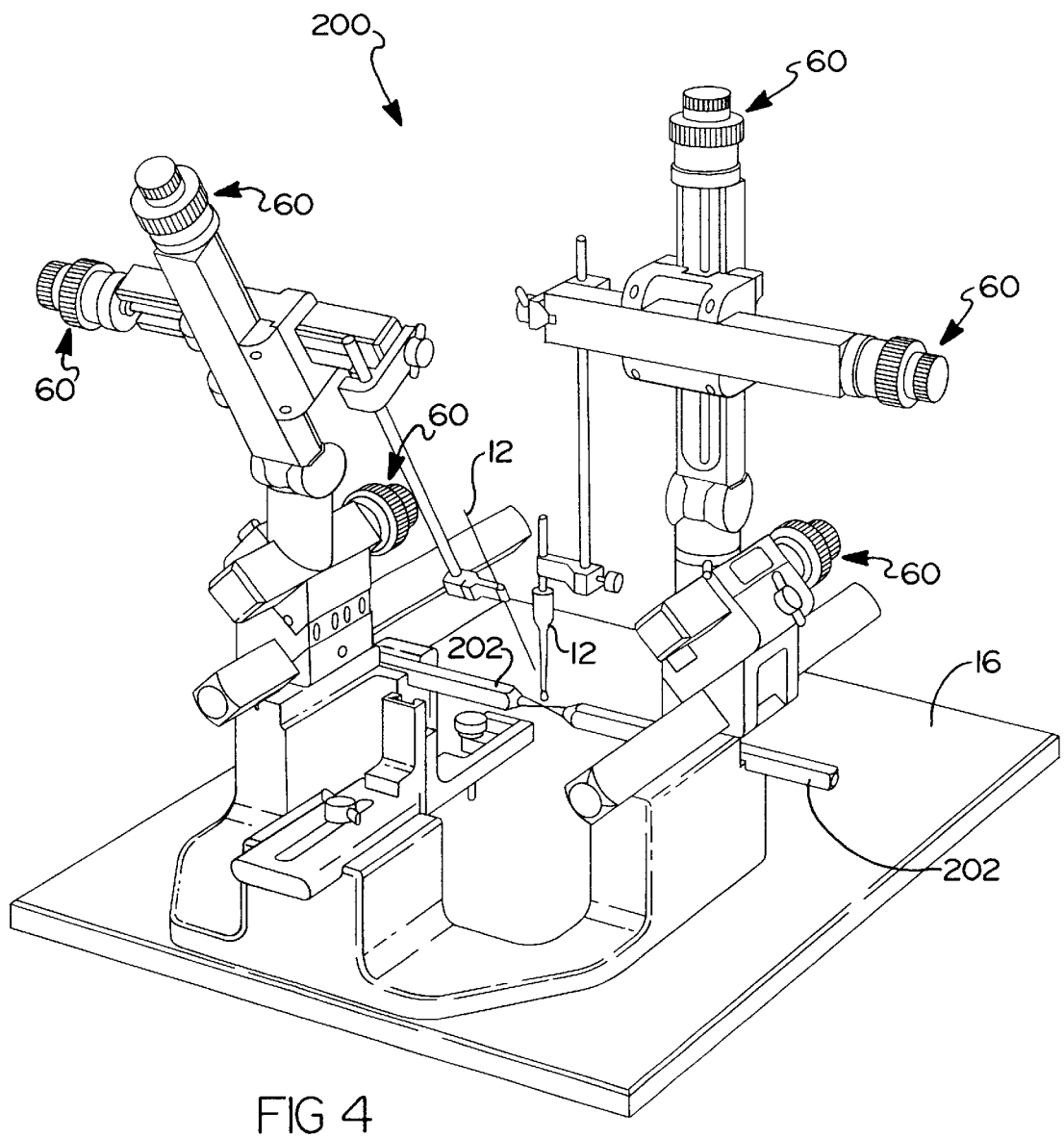
FIG. 4 is a perspective view of a stereotaxic system provided with a plurality of dual drive positioning systems constructed in accordance with the invention.

Another example of an application of the dual drive system described above is shown in FIG. 4 wherein a stereotaxic device 200 of generally known construction is provided with dual drive systems 60 of the type described above. The stereotaxic device 200 is designed to hold a laboratory animal in a fixed position with ear bars 202 which engage within the animal's ears during various laboratory procedures.

There has been disclosed heretofore the best embodiment of the invention presently contemplated. However, it is to be understood that the various changes and modifications may be made thereto without departing from the spirit of the invention.

What is claimed is:

1. A dual drive system for a positioning apparatus, comprising:
   a slide adapted to carry an instrument;
   a drive member connected to said slide;
   a pinion gear provided on said drive member;
   a first hand operated drive wheel fixed to said drive member;
   a second hand operated drive wheel carried by said slide;
   a ring gear mounted on said second drive wheel; and
   a gear train rotationally coupling said ring gear and said pinion gear.

2. The system of claim 1, wherein said drive member comprises a drive shaft and wherein said first and second drive wheels are each concentrically mounted around said drive shaft.

3. The system of claim 1, wherein said gear train comprises an idler gear engaged with said pinion gear and a spur gear engaged with said ring gear.

4. The system of claim 3, wherein said idler gear and said spur gear are engaged with one another.

5. The system of claim 1, further comprising a bearing housing carried by said slide, a bearing mounted on said bearing housing and said second drive wheel rotatably mounted on said bearing housing by said bearing.

6. The system of claim 1, further comprising a bearing housing carried by said slide, at least one bearing mounted on said bearing housing and rotatably supporting said drive member on said bearing housing.

7. The system of claim 1, further comprising a plurality of anchor posts carried by said slide, and wherein said gear train is mounted on said anchor posts.

8. The system of claim 7, further comprising a cover plate fixed to said anchor posts.

9. The system of claim 1, further comprising a cover plate carried by said slide and located between said first and second drive wheels.

10. A precision positioning apparatus, comprising:
    a base;
    a slide assembly supported on said base;
    an instrument carried by said slide assembly; and
    a hand operated dual drive system for accurately moving said instrument along said slide assembly;
    said dual drive system comprising an axially movable drive shaft connected to said slide assembly, and first and second drive wheels connected to said drive shaft such that said first and second drive wheels and said drive shaft each rotate together in a common direction.

11. The apparatus of claim 10, wherein said first drive wheel is directly connected to said drive shaft.

12. The apparatus of claim 11, further comprising a plurality of gears interconnecting said second drive wheel to said drive shaft.

13. The apparatus of claim 10, wherein said first and second drive wheels are each coaxially mounted around said drive shaft.

14. The apparatus of claim 10, wherein said first and second drive wheels are closely axially juxtaposed.

15. The apparatus of claim 10, further comprising a ring gear mounted on said first drive wheel and a pair of gears interconnecting said ring gear with said shaft.

16. The apparatus of claims 15, further comprising a pinion gear carried on said drive shaft engaged with one of said pair of gears.

17. The apparatus of claim 15, further comprising a pair of anchor posts fixed to said slide assembly and respectively rotationally supporting said pair of gears.

18. The apparatus of claim 17, further comprising a cover plate mounted on said pair of anchor posts.

19. The apparatus of claim 10, wherein said apparatus comprises a micromanipulator.

20. The apparatus of claim 10, wherein said apparatus comprises a stereotaxic device.

* * * * *